(12) United States Patent
Leschik

(10) Patent No.: US 8,574,250 B2
(45) Date of Patent: Nov. 5, 2013

(54) EAR CANDLE

(76) Inventor: Udo Leander Leschik, Schöffengrund-Schwalbach (DE)

( * ) Notice: Subject to any disclaimer, the term of this patent is extended or adjusted under 35 U.S.C. 154(b) by 0 days.

(21) Appl. No.: 13/814,301

(22) PCT Filed: Nov. 8, 2011

(86) PCT No.: PCT/EP2011/069683
§ 371 (c)(1),
(2), (4) Date: Apr. 25, 2013

(87) PCT Pub. No.: WO2012/062774
PCT Pub. Date: May 18, 2012

(65) Prior Publication Data
US 2013/0218182 A1    Aug. 22, 2013

(30) Foreign Application Priority Data
Nov. 11, 2010 (EP) .................................. 10190810

(51) Int. Cl.
*A61F 9/00* (2006.01)

(52) U.S. Cl.
USPC ........................................ 606/162

(58) Field of Classification Search
USPC ............... 606/162; 128/864; 604/1; D24/106, D24/151, 108
See application file for complete search history.

(56) References Cited

FOREIGN PATENT DOCUMENTS

| DE | 10 2006 004 138 A1 | 8/2007 |
|----|---|---|
| EP | 0 908 161 A1 | 4/1999 |
| FR | 2 768 924 A1 | 4/1999 |

OTHER PUBLICATIONS

International Search Report and Written Opinion of the International Searching Authority for International Application No. PCT/EP2011/069683, dated Dec. 12, 2011.

*Primary Examiner* — Ryan Severson
*Assistant Examiner* — Anh Dang
(74) *Attorney, Agent, or Firm* — McCarter & English, LLP

(57) ABSTRACT

Ear candle with an air-permeable retaining member disposed at least partially within the ear candle, wherein the retaining member comprises a wall and an interior space, wherein at least two lamellas directed into the interior space are disposed on the wall, wherein the at least two lamellas are disposed opposite from each other in the interior space, and wherein the at least two lamellas are configured so as to overlap in the axial direction.

14 Claims, 5 Drawing Sheets

EAR CANDLE

CROSS-REFERENCE TO RELATED APPLICATIONS

This application is the U.S. National Phase of International Application No. PCT/EP2011/069683, filed Nov. 8, 2011, which, in turn, claims priority to European Application No. EP 10190810.1, filed Nov. 11, 2010, the contents of both of which are hereby incorporated by reference in their entirety as part of the present disclosure.

FIELD OF THE INVENTION

The invention relates to an ear candle with an air-permeable retaining member disposed within the ear candle.

BACKGROUND OF THE INVENTION

An ear candle with an integrated retaining member, wherein the retaining member is disposed within the ear candle at a rear end, i.e. at an end of the ear candle at the side of the ear, is part of the prior art (DE 10 2006 004 138 A1).

This retaining member is an air-permeable retaining member having a cross-sectional surface area which has the shape of a pointed cone or a frustrum of a cone or a dome or a pitched roof or a pyramid or a hollow cylinder, the point or the frustrum or the curvature of this retaining member being oriented towards a front end of the ear candle.

The ear candle substantially consists of a cotton fabric impregnated with wax. The wax used can be a natural wax such as beeswax, for instance. It is also possible to use synthetic waxes such as stearin or paraffin. However, natural waxes are preferred. The cotton fabric is rolled into a tube in such a way that, during rolling, at least one layer of the fabric overlaps or that several layers of the fabric lie one on top of the other.

With one end, this tube is placed on the external ear canal and the other end is set alight so that an open flame is produced.

The action of the ear candles is purely physical. A slight negative pressure (chimney effect) and the vibration waves of the air in the candle caused by the movement of the flame act like a gentle massage of the eardrum. This leads to an intense feeling of pleasant warmth and a pressure equalization in the area of the ears, the frontal and nasal sinuses that is perceived as liberating.

The amount of wax in the cotton fabric is adapted to the combustion process. This means that optimally, the ear candle is supposed to burn as residue-free as possible.

A plume of ash, which usually snaps off at the end, is left during burning.

A gas mixture is produced inside the ear candle. The gas mixture cools off in the ear candle, falls down, condensates and would enter the external ear canal unimpeded but for the retaining member.

Moreover, when the ear candle burns down, the wax melts. In rare cases, if too large an amount of wax is provided, the wax may also flow downwards in the ear candle and would enter the external ear canal but for the retaining member.

The ear candle with a retaining member described in the prior art (DE 10 2006 004 138 A1) is disadvantageous in that the retaining member described therein either does not sufficiently retain the condensate produced and possible run-off wax, depending on what material the retaining member consists of, for example, if it consists of a fly screen or a fine-mesh wire. If the retaining member consists of a filter paper or a filter fabric, it will easily clog so that air-permeability is not ensured any more.

SUMMARY OF THE INVENTION

The technical problem underlying the invention consists of proposing an ear candle with a retaining member that reliably prevents condensate and possible run-off wax from running further, and which, furthermore, ensures an air-permeability of the retaining member even in the case of larger amounts of condensate and wax.

The ear candle according to the invention with an air-permeable retaining member disposed at least partially within the ear candle, wherein the retaining member comprises a wall and an interior space, is characterized in that at least two lamellas directed into the interior space are disposed on the wall, and that the at least two lamellas are configured so as to overlap in the axial direction.

Due to the embodiment according to the invention of the retaining member in the ear candle, it is ensured that condensate and possible run-off wax is very reliably prevented in the retaining member from running further. The retaining member according to the invention does not clog even given larger amounts of condensate and wax, so that air-permeability is ensured.

Advantageously, the lamellas are configured so as to rest flush on the wall with their side facing the wall. They rest against the wall of the retaining member at least in a semicircular shape. Moreover, they protrude over a center line of the retaining member. The lamellas cover more than half of the opening of the retaining member.

The at least two lamellas are configured so as to overlap in the axial direction. Due to the fact that the at least two lamellas are disposed opposite from each other in the interior space, the retaining member, seen in the axial direction, is visually tight so that even dropping condensate or dropping wax is caught by the lamellas.

According to a particularly preferred embodiment, at least three lamellas are disposed in the retaining member, with at least one lamella being disposed opposite the other lamellas and configured so as to overlap them in the axial direction. The retaining member is visually tight, seen in the axial direction, also with three lamellas, so that even dropping wax or condensate is unable to enter the external ear canal but is caught by the lamellas.

According to another advantageous embodiment of the invention, the retaining member has at least one opening in a jacket surface. The retaining member according to the invention is thus easier to produce if it is formed as an injection-molded member.

According to another advantageous embodiment of the invention, the at least one opening is disposed in the area of the at least one lamella. The material which would otherwise form the wall of the retaining member in the area of the opening is thus used for forming the lamella.

Advantageously, the at least two lamellas are disposed at an angle of 30° to 60° in the retaining member. According to a particularly preferred embodiment, the at least two lamellas are disposed at an angle of 45° in the retaining member. It is thus ensured that, on the one hand, the lamellas overlap in such a way that the retaining member, seen in the axial direction, is visually tight, so that no condensate or wax is able to enter into the external ear canal, and that on the other hand, the retaining member is provided with a sufficient passage of air.

A development of the invention provides that the retaining member comprises a nozzle for fitting on the external ear canal (fitting nozzle) that has a diameter that widens towards the ear candle. It is thus ensured that the retaining member can be fitted onto the ear canal easily and injury-free with the fitting nozzle. A development with rounded external surfaces of the fitting nozzle ensures that there are no sharp edges and that thus, the skin is not injured. Moreover, the feel of the ear candle is significantly improved.

In the direction of the ear candle, the fitting nozzle advantageously has a projecting portion that corresponds to the thickness of the material of the ear candle. Thus, the fitting nozzle, which is partially disposed in the ear candle and partially protrudes over the ear candle, ends flush with a sleeve of the ear candle. As was already explained, the ear candle consists, for example, of a cotton fabric impregnated with beeswax. This cotton fabric is rolled to form the ear candle, so that the ear candle has a cavity inside. The sleeve of the ear candle thus consists of a single- or multi-layered cotton fabric impregnated with beeswax.

As was already explained, the fitting nozzle advantageously protrudes over the ear candle in the axial direction. It is thus ensured that the ear candle can be fitted onto the external ear canal with the fitting nozzle of the retaining member without there being any danger of injury to the skin.

The retaining member is preferably configured in the shape of a cylinder or a section of a cone. It is thus possible to insert the retaining member into the pre-fabricated ear candle in a simple manner.

Advantageously, the retaining member is retained in the ear candle without any additional adhesive means in a clamping manner.

The retaining member advantageously consists of plastic, glass, ceramics, wood and metal. A particularly preferred embodiment provides to form the retaining member from plastic. Polypropylene (PP) is preferably used as the plastic. However, it is also possible to use polypropylene carbonate (PPC) or polyethylene (PE). It is also possible to provide a mixture.

Further features and advantages of the invention are apparent from the associated drawing in which several exemplary embodiments of the retaining member according to the invention of an ear candle are illustrated only by way of example.

DETAILED DESCRIPTION OF EMBODIMENTS OF THE INVENTION

Figure 1:
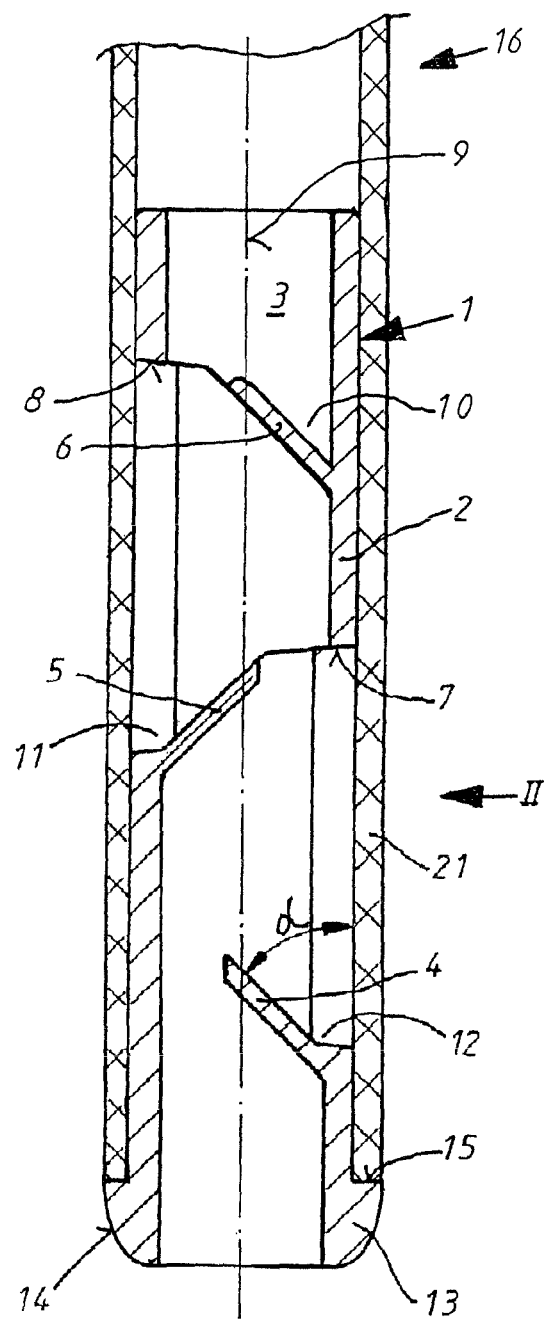
FIG. 1 shows a longitudinal section through a retaining member with three lamellas.

FIG. 1 shows a retaining member 1 comprising a wall 2 and an interior space 3. Three lamellas 4, 5, 6 disposed at an angle α of 45° are disposed in the interior space.

Openings 7, 8 are disposed in the retaining member in the area of the lamellas 4, 5.

As can be seen from the drawn-in center line 9, the lamellas 4, 5, 6 respectively protrude over the center line 9, i.e. the lamellas 4, 5, 6 overlap, seen in the axial direction, so that the retaining member is configured to be visually tight, seen in the axial direction. It is thus ensured that 100% of the condensate and possible run-off wax is caught by the retaining member.

The run-off wax collects, in particular, in the depressions 10, 11, 12. In turn, this means that the passage of air in the retaining member is not affected by the collecting condensate and wax.

The retaining member comprises a fitting nozzle 13 which comprises a rounded external surface 14. Furthermore, the fitting nozzle 13 comprises a projecting portion 15 in such a way that the retaining member 1 ends flush with a sleeve 21 of an ear candle 16. The retaining member 1 is partially disposed in the sleeve 21 of the ear candle 16 and protrudes with the fitting nozzle 13.

Figure 2:
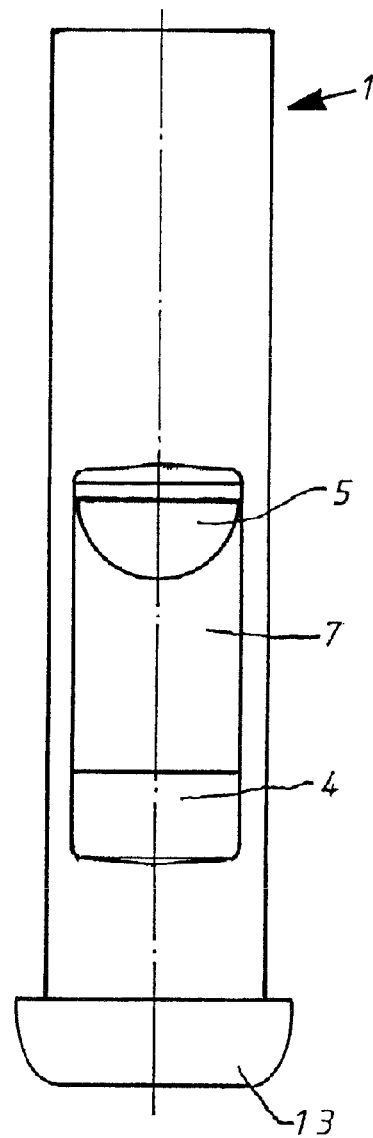
FIG. 2 shows a view in the direction of the arrow II of FIG. 1 (without the part 21)

FIG. 2 shows the retaining member 1 with the fitting nozzle 13 and the opening 7 as well as the lamellas 4 and 5. For a better overview, the sleeve 21 is not shown in FIG. 2.

Figure 3:
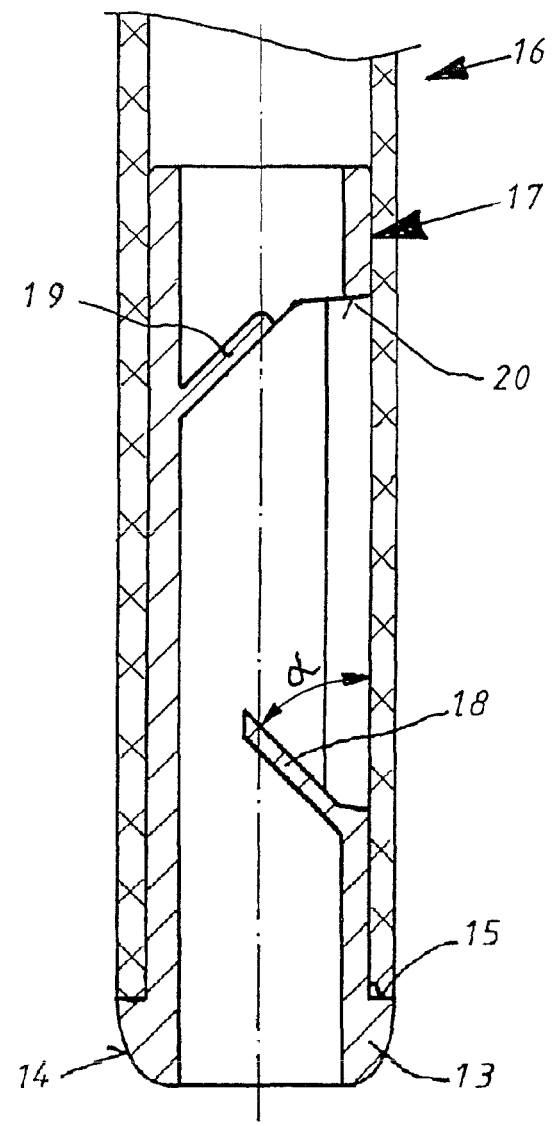
FIG. 3 shows a longitudinal section through a retaining member with two lamellas.

FIG. 3 shows a retaining member 17 comprising two lamellas 18, 19. The retaining member 17 is disposed in the ear candle 16. The lamellas 18, 19 also overlap, so that run-off condensate and even dropping condensate and wax is unable to pass through the retaining member in the direction of the ear (not shown).

The retaining member 17 comprises an opening 20 disposed in the area of the lamellas 18, 19.

Figure 4:
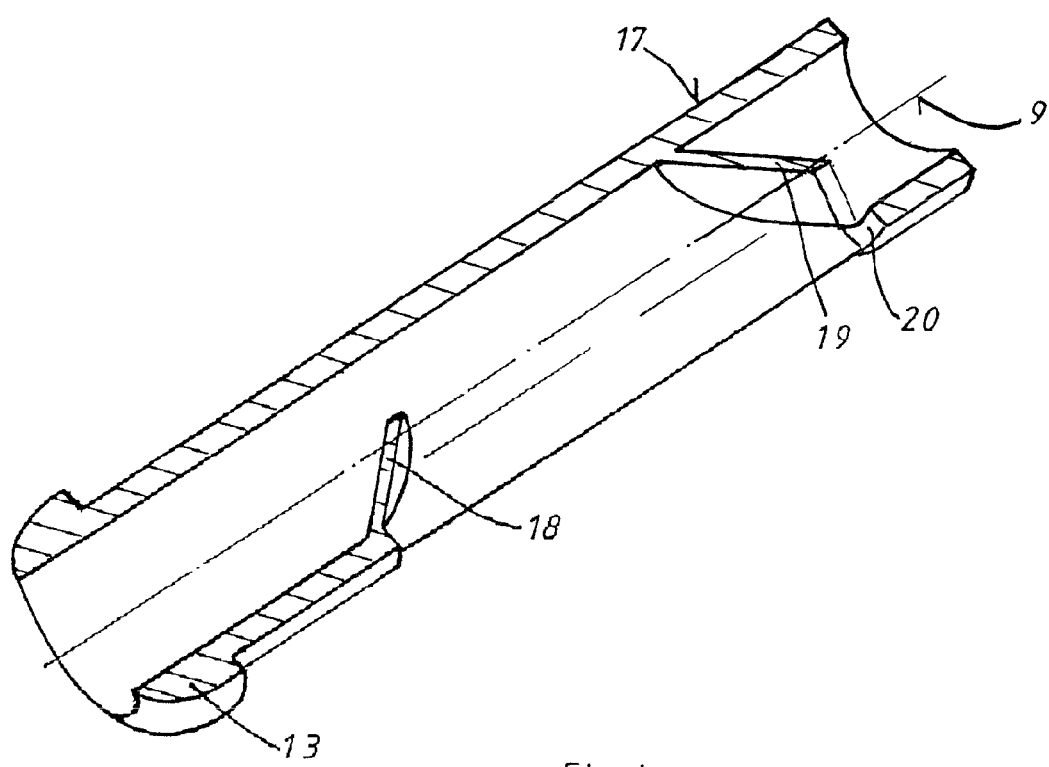
FIG. 4 shows a retaining member with two members in a perspective view, cut open longitudinally.

FIG. 4 shows the retaining member 17 with the lamellas 18, 19 and the opening 20.

The fitting nozzle 13, which has the same configuration and function as in the embodiment according to FIGS. 1 and 2, is shown in FIGS. 3 and 4.

Figure 5:
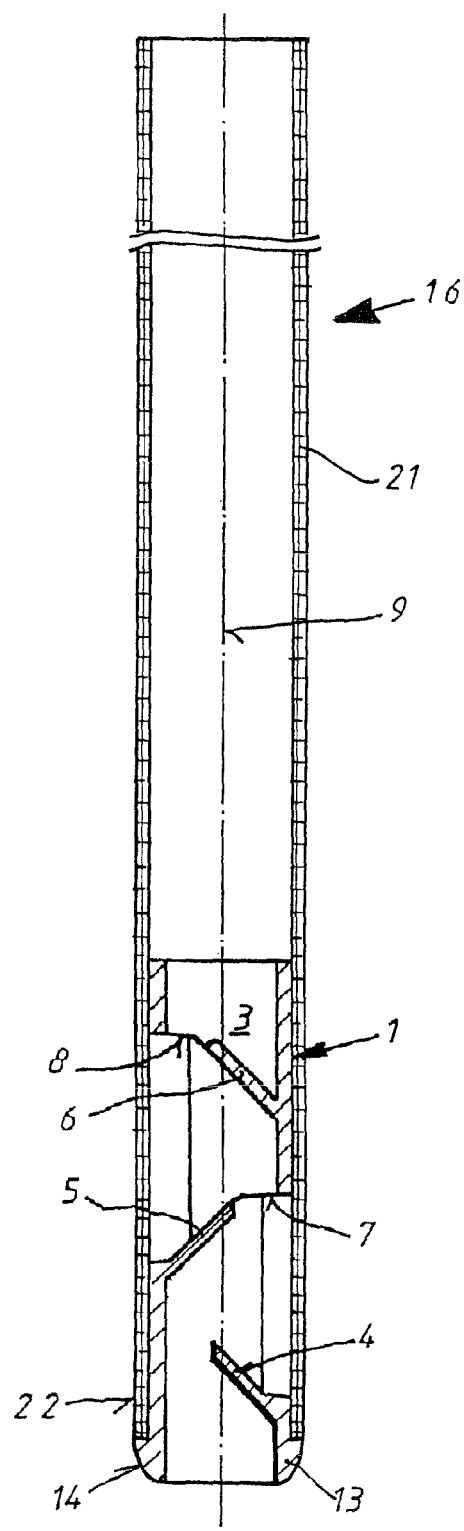
FIG. 5 shows a longitudinal section through an ear candle with a retaining member.

FIG. 5 shows the ear candle 16 with the sleeve 21, which consists of a cotton fabric impregnated with beeswax. The retaining member 1 is disposed in the part 22 of the ear candle 16 on the side of the ear. The retaining member 1 comprises the lamellas 4, 5, 6 as well as the openings 7, 8 that are sealed by the sleeve 21.

Furthermore, the retaining member 1 comprises the fitting nozzle 13 so that the ear candle can be placed injury-free, with a significantly improved feel.

The invention claimed is:

1. A device comprising:
    an ear candle; and
    an air-permeable retaining member disposed at least partially within the ear candle, wherein the retaining member comprises a wall, an interior space, and at least two lamellas, wherein
    the at least two lamellas are disposed on the wall and extend in a direction into the interior space,
    the at least two lamellas are disposed opposite from each other in the interior space, and
    the at least two lamellas are configured so as to overlap in an axial direction.

2. A device as defined in claim 1, wherein the at least two lamellas comprise at least three lamellas, and at least one of the at least three lamellas is disposed opposite from the other of the at least three lamellas in the interior space and is configured so as to overlap with the other of the at least three lamellas in the axial direction.

3. A device as defined in claim 1, wherein the retaining member has at least one opening in the wall.

4. A device as defined in claim 3, wherein the at least one opening is disposed in an area of the wall adjacent at least one of the at least two lamellas.

5. A device as defined in claim 1, wherein the at least two lamellas are each disposed in the retaining member at an angle of about 30° to about 60° from the wall.

6. A device as defined in claim 5, wherein the at least two lamellas are each disposed in the retaining member at an angle of about 45° from the wall.

7. A device as defined in claim 1, wherein the at least two lamellas are each disposed flush with and at least in a semi-circular shape on the retaining member.

8. A device as defined in claim 1, further comprising a fitting nozzle defining a diameter, wherein the diameter increases in a direction towards the ear candle.

9. A device as defined in claim 8, wherein the fitting nozzle comprises a rounded external surface.

10. A device as defined in claim 8, wherein the ear candle comprises a sleeve defining a thickness thereof, and wherein the fitting nozzle includes a projecting portion external and adjacent to the ear candle, defining a dimension corresponding to the thickness of the sleeve.

11. A device as defined in claim 8, wherein the fitting nozzle is configured to protrude past the ear candle in the axial direction.

12. A device as defined in claim 1, wherein the retaining member is configured in the shape of a cylinder or a section of a cone.

13. A device as defined in claim 1, wherein the retaining member is formed from plastic, glass, ceramics, wood or metal.

14. A device as defined in claim 1, wherein the retaining member is formed from polypropylene (PP), polypropylene carbonate (PPC) and/or polyethylene (PE).

\* \* \* \* \*